United States Patent [19]

Klein et al.

[11] 4,340,363

[45] Jul. 20, 1982

[54] ORTHODONTIC ROTATION WEDGE WITH TWIST-PREVENTING MOUNDS

[75] Inventors: Paul E. Klein, Lake Oswego; Roland M. Anderson, Portland, both of Oreg.

[73] Assignee: Modcom, Inc., Canby, Oreg.

[21] Appl. No.: 229,769

[22] Filed: Jan. 29, 1981

Related U.S. Application Data

[63] Continuation of Ser. No. 6,583, Jan. 26, 1979, abandoned.

[51] Int. Cl.³ .............................................. A61C 3/00
[52] U.S. Cl. ......................................... 433/18; 433/16
[58] Field of Search ............................. 433/18, 16, 11

[56] References Cited

U.S. PATENT DOCUMENTS

| | | | |
|---|---|---|---|
| 3,218,715 | 11/1965 | Wallshein | 433/16 |
| 3,879,850 | 4/1975 | Wallshein | 433/18 |
| 3,896,549 | 7/1975 | Wallshein | 433/18 |
| 3,913,228 | 10/1975 | Wallshein | 433/18 |
| 4,054,997 | 10/1977 | Wallshein | 433/18 |

*Primary Examiner*—Gene Mancene
*Assistant Examiner*—John J. Wilson
*Attorney, Agent, or Firm*—Kolisch, Hartwell & Dickinson

[57] ABSTRACT

An orthodontic tooth-rotation-effecting wedge. The wedge is made of a mouth-fluid-resistant elastomeric material. It includes a relatively thin web having a pair of openings for releasably fitting over and encircling a pair of conventional bracket posts, and a bulge, or enlargement, joined to one side of the web. The bulge is for deflecting an arch wire from the path which, in the absence of installation of the wedge, it would normally tend to follow past a bracket. A pair of spaced mounds is formed on one side of the enlargement. These mounds are adapted to straddle an arch wire to prevent twisting of the wedge out of place.

2 Claims, 4 Drawing Figures

ORTHODONTIC ROTATION WEDGE WITH TWIST-PREVENTING MOUNDS

CROSS-REFERENCE TO RELATED APPLICATION

This is a continuation of our prior-filed copending application entitled "Orthodontic Rotation Wedge With Twist-Prevention Mounds", Ser. No. 006,583, filed Jan. 26, 1979, now abandoned.

BACKGROUND AND SUMMARY OF THE INVENTION

This invention pertains to an orthodontic wedge which is used to effect rotation of a tooth about its own longitudinal axis.

Among the many corrective actions and movements which are used during different orthodontic treatment plans is rotation of a tooth about its own axis. There are a number of instances in which it is desirable to accomplish this kind of action through the use of what is known as a rotational wedge. In general terms, such a device acts between the tooth and a force-effecting arch wire, on one side of the tooth, to create the intended rotation-producing force on the tooth.

As an illustration of a circumstance wherein the use of a wedge is desirable, it is sometimes the case that a bracket which is used to tie in an arch wire to a tooth is not properly located, in an angular sense, relative to the tooth's longitudinal axis, whereby effective rotation cannot be imparted without the use of a wedge. In other words, and during an orthodontic program, it may be discovered that more of a rotational force is required on a tooth than can be achieved without shifting the angular position of the bracket thereon, or using a wedge. Shifting of a bracket is time-consuming and costly, and is usually sought to be avoided.

Another instance where a wedge of the type indicated is extremely helpful is in the case where a tooth's initial orientation in a mouth is considerably rotated in one direction, and requires rather severe correction. Such a tooth often has a tendency, even after the completion of orthodontic treatment, to re-rotate or return toward the angular rotational position which it initially had. To take care of this situation it is often desirable to over-rotate the tooth in the opposite direction, so that when it tends to return, it will tend to return toward a correct angular position. Such over-rotation as a corrective action is most easily accomplished using a rotational wedge.

Further, it is sometimes the case that an orthodontist is not able to tell initially from a tooth's anatomy what should be the proper angular positioning of a bracket relative to the tooth's axis. In other words, he may suspect from the beginning that wherever he places the bracket relative to the tooth's axis, there will come a time when a rotational force is necessary, and the bracket will at that time not be in a proper position. Obviously, a wedge is quite helpful in this situation.

A general object of the present invention, therefore, is to provide a uniquely configured and constructed rotation wedge conveniently usable for all of the above-mentioned purposes, as well as for many others.

Another object of the invention is to provide such a wedge which is simple in construction and easy to install and use.

Still a further object of the invention is to provide a wedge of the type generally indicated which is reliably effective over extended periods of time in a person's mouth.

According to a preferred embodiment of the invention, the wedge is made of a mouth-fluid-resistant elastomeric material, such as a urethane resin material. It includes a thin, generally planar web portion having a pair of openings for releasably fitting over and encircling a pair of conventional orthodontic bracket posts. Joined integrally with the web portion is a thick bulge portion, or enlargement, which extends along one side of the web portion. With the wedge properly fitted in place, the enlargement therein is disposed at an outer set of sides of the posts to which the web portion is attached, and the enlargement acts to deflect an attached arch wire out of the path which it would normally follow through the usual arch wire slot defined in the bracket.

Formed on the outside and outwardly facing surface of the enlargement are two projecting mounds, or projections, which are spaced apart so as to straddle and engage opposite sides of an arch wire. These mounds function to prevent angulation or twisting of the wedge out of a position where the bulge portion can act effectively against the wire.

These and other objects and advantages which are attained by the invention will become more fully apparent as the description which now follows is read in conjunction with the accompanying drawings.

DETAILED DESCRIPTION OF THE INVENTION

Figure 1:
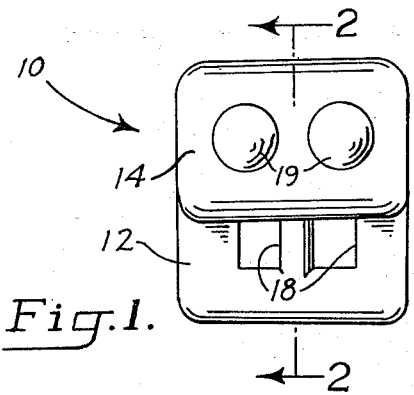
FIG. 1 is a side view of a rotational wedge made in accordance with the present invention.
Figure 2:
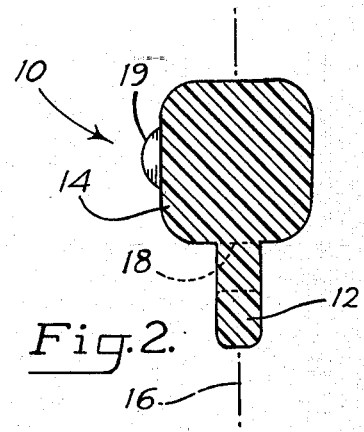
FIG. 2 is a cross-sectional view taken along line 2—2 in FIG. 1.

Turning now to the drawings, and referring first to FIGS. 1 and 2, indicated generally at 10 is an orthodontic rotational wedge made in accordance with the present invention. Wedge 10 is a unitary device, preferably molded from a mouth-fluid-resistant elastomeric material, such as a thermoset-thermoplastic, polyester-based, isocyanate-terminated, urethane resin. Resins of this type are commercially available.

Wedge 10 includes a substantially planar web, or tab, 12 which joins integrally with an enlargement, or bulge portion, 14. The cross-sectional configuration of enlargement 14, and its disposition relative to the plane 16 of web 12, are clearly illustated in FIG. 2. More specifically, it will be seen in FIG. 2 that the enlargement projects normally from opposite sides of web 12. Web 12 constitutes a an attaching portion herein, said enlargement 14 constitutes a displacing portion.

Formed at the locations clearly illustrated in FIG. 1, within web 12, are two apertures, or void spaces, 18. These apertures functon as will below be described to attach wedge 10 to a pair of posts in a conventional type of standard-twin orthodontic bracket. Further, formed on one face of enlargement 14 which may be thought of as the outer face in the enlargement, are two mounds or projections 19 spaced apart as shown. The function of these mounds will also be explained below.

Figure 4:
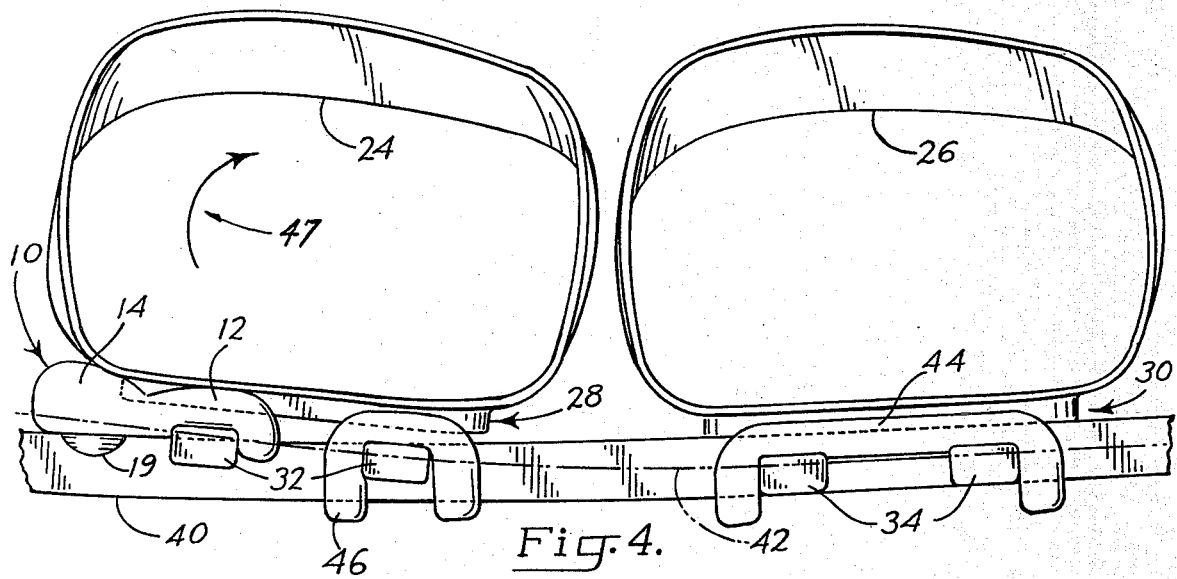
FIG. 4 is a fragmentary view taken from the top side of FIG. 3.
Figure 3:
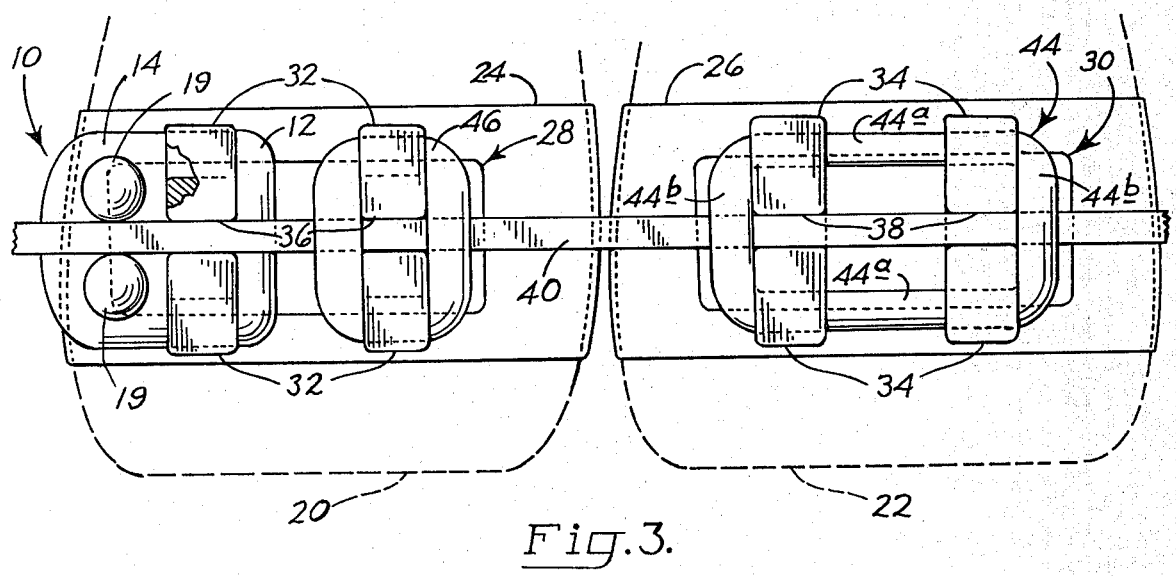
FIG. 3 is a fragmentary front elevation illustrating installed orthodontic apparatus using the wedge of FIGS. 1 and 2.

FIGS. 3 and 4 in the drawings illustrate wedge 10 mounted in an operative position with other orthodontic apparatus. Referring to these two figures, two adjacent upper teeth are represented by dashed lines 20, 22 in FIG. 3. These teeth have, for the sake of clarity, been omitted in FIG. 4. Conventionally mounted, as by cementing, on tooth 20 is a metallic orthodontic band 24. A similar band 26 is likewise mounted on tooth 22. Conventionally anchored as by welding on the front sides of bands 24, 26 are what are known as standard-twin orthodontic brackets 28, 30, respectively. The relative angular orientations of teeth 20, 22 are reflectd by the relative angular orientations of bands 24, 26, respectively, as shown in FIG. 4. Bracket 28 includes a set of four conventional ligating posts 32, and bracket 30 includes a similar set of posts 34.

The posts in brackets 28, 30 define generally horizontal slots 36, 38, respectively, for receiving an orthodontic arch wire, such as arch wire 40. More specifically, and with reference especially to FIG. 4, with the bands and brackets oriented as indicated, slots 36, 38 define what might be thought of as a curvilinear nominal path, represented by dash-double-dot line 42, for wire 40 with the same held in the slots tightly against the brackets.

The stretch of wire 40 which extends along slot 38 is held therein by an elastic ligating loop 44. As can be seen, loop 44 includes runs 44a which extend behind posts 34, and runs 44b which extend over the front side of the arch wire at either side of bracket 30. Loop 44 herein is made of substantially the same material used for wedge 10, and may be constructed in accordance with the loop ligating device shown and described in U.S. Pat. No. 3,530,583.

Where wire 40 extends past posts 32 in bracket 28, it is held in the right-end portion of slot 36 in the figures by a ligating loop 46 which extends as shown over the front sides of the arch wire, and over the rear sides of the two right-hand posts 32 in the figures. Loop 46 is substantially the same in construction as loop 44.

FIGS. 3 and 4 illustrate a situation in which it has been decided to produce axial rotation of tooth 20 in the direction of arrow 47 in FIG. 4. Accordingly, wedge 10 is fitted as shown on the two left-hand posts 32 in FIGS. 3 and 4. More specifically, apertures 18 in web 12 have been fitted over these two posts to encircle or capture the same, and thus to attach the wedge against rotation, with enlargement 14 extending along the left sides of the posts. It will be apparent that with this kind of fitment, wedge 10 is securely held in place without the necessity of using any other device to anchor it.

As can be seen especially in FIG. 4, enlargement 14, with the wedge installed, at least partially blocks the nominal path through slot 38 represented by dash-double-dot line 42. As a consequence, arch wire 40 is displaced outwardly from this path adjacent the left side of tooth 20 in the figures—namely where the wire passes over enlargement 14. Wire 40, where it passes over this enlargement, has a tendency to return toward path 42, and thus presses against the enlargement, and hence against the tooth in a manner tending to rotate it axially in the direction of arrow 47.

Looking at FIGS. 3 and 4 together, it will be noted that where wire 40 extends over enlargement 14, it passes between mounds 19. These mounds, through acting against the upper and lower sides of the wire, prevent the enlargement in the wedge from angulating or twisting (about an axial substantially normal to the plane of FIG. 3, such plane corresponding to the plane of web 12) out of a proper operative position.

It will thus be apparent that an extremely simple and easily used rotational wedge is proposed by the invention. The wedge requires no special additional equipment to mount it in place, inasmuch as it is provided with a web having apertures shaped for capturing fitment over conventional bracket posts. It is readily mounted and demounted as required, and is bidirectionally functional. In other words, it can be used in a reverse direction on a "right-hand" set of posts to produce axial tooth rotation in the direction opposite that indicated by arrow 47. The material used to make up the wedge is capable of providing long-lasting rotational force-transmission, in a manner which is gradual, gentle and effective. The enlargement in the wedge may, of course, be provided in various different sizes to effect different amounts of rotational force. Mounds, such as mounds 19, inhibit twisting of the wedge.

While a preferred embodiment of the invention has been described herein, it is appreciated that variations and modifications may be made without departing from the spirit of the invention.

It is claimed and desired to secure by Letters Patent:

1. A mouth-fluid resistant elastomeric tooth rotation-effecting device in combination with a standard-twin-type orthodontic bracket or the like having at least one pair of ligation posts disposed on opposite sides of and at least partially defining a path for receiving an orthodontic arch wire, said device comprising an attaching portion in the form of a substantially planar web of one cross-sectional thickness including, in the plane of the web, a pair of apertures releasably receiving and encircling such posts, said apertures, as so encircling such posts, inhibiting rotation of the device relative to such a bracket about an axis normal to the plane of said web, a displacing portion having a cross-sectional thickness greater than said one thickness joined to one side, and in the plane, of said web and being sized whereby, with said apertures releasably receiving and encircling the posts in the bracket, said displacing portion extends at least partially across the wire-receiving path in the bracket for the purpose of exerting a tooth-rotating force in a direction generally normal to said plane, and a pair of spaced projections joined to and projecting from one side of said displacing portion, adapted laterally to straddle an arch wire with the device in place with respect to such a wire and bracket, said projections, when so straddling an arch wire, being positioned to react, through direct lateral contact, with the arch wire thus to inhibit lateral shifting of said displacing portion relative to the arch wire, and to insure retention of the arch wire in the space between said projections.

2. The device of claim 1, wherein said displacing portion, when viewed in the plane of said web, projects in a direction normal to said plane beyond said web on at least one side of such plane.

* * * * *